United States Patent
Sarwal et al.

(10) Patent No.: US 6,473,652 B1
(45) Date of Patent: Oct. 29, 2002

(54) METHOD AND APPARATUS FOR LOCATING IMPLANTED RECEIVER AND FEEDBACK REGULATION BETWEEN SUBCUTANEOUS AND EXTERNAL COILS

(75) Inventors: Alok Sarwal, Highlands Ranch, CO (US); Birinder R. Boveja, Highlands Ranch, CO (US)

(73) Assignee: NAC Technologies Inc., Milkwaukee, WI (US)

( * ) Notice: Subject to any disclaimer, the term of this patent is extended or adjusted under 35 U.S.C. 154(b) by 0 days.

(21) Appl. No.: 09/532,931

(22) Filed: Mar. 22, 2000

(51) Int. Cl.7 ................................................ A61N 1/08
(52) U.S. Cl. ............................ 607/62; 607/61; 607/60
(58) Field of Search ................................ 128/903, 901; 607/2, 27, 30, 31, 32, 33, 46, 50, 39, 40, 55, 60, 61, 62

(56) References Cited

U.S. PATENT DOCUMENTS

| | | | | |
|---|---|---|---|---|
| 3,796,221 A | * | 3/1974 | Hagfors | 607/40 |
| 4,352,960 A | | 10/1982 | Dormer et al. | 179/107 |
| 5,117,825 A | | 6/1992 | Grevious | 128/419 |
| 5,314,453 A | | 5/1994 | Jeutter | 607/61 |
| 5,324,315 A | * | 6/1994 | Grevious | 128/903 |
| 5,545,191 A | | 8/1996 | Mann et al. | 607/57 |
| 5,749,909 A | * | 5/1998 | Schroeppel et al. | 607/33 |
| 5,764,052 A | * | 6/1998 | Renger | 324/253 |
| 5,811,893 A | | 9/1998 | Soyck | 307/116 |
| 5,843,139 A | * | 12/1998 | Goedeke et al. | 128/903 |
| 5,948,006 A | * | 9/1999 | Mann | 128/903 |
| 6,101,417 A | * | 8/2000 | Vogel et al. | 607/30 |

* cited by examiner

Primary Examiner—Kennedy Schaetzle

(57) ABSTRACT

A method and apparatus for proximity sensing and feedback regulation between a bodily implanted secondary coil and an external primary coil applied for generating and propagating a well-defined set of excitation signals used for nerve or muscle stimulation. The complete device is a combination of external and implantable or internal components. The internal component contains a relatively small magnet composed of materials that exhibit Giant Magneto-resistor characteristics, passive circuitry and a secondary coil. The external coil contains proximity sensor circuitry that is rigidly connected in a convenient enclosure mounted supercutaneously. Feedback information of the position of the implanted coil is provided to the pulse generation circuit and the parameters are adjusted to compensate for any variation in the position of the internal coil in order to maintain the necessary signal pattern.

24 Claims, 10 Drawing Sheets

METHOD AND APPARATUS FOR LOCATING IMPLANTED RECEIVER AND FEEDBACK REGULATION BETWEEN SUBCUTANEOUS AND EXTERNAL COILS

FIELD OF THE INVENTION

The present invention relates to communication between a subcutaneously implanted lead-receiver and external transmitter. More specifically, the present invention relates to a proximity sensing and feedback regulation system for the reliable generation and propagation of programmed pulse excitation signals to an implant from an external controller by use of inductive fields. These excitation signals are used for stimulating excitable tissue, such as a nerve bundle or muscle.

BACKGROUND OF THE INVENTION

There is mounting scientific evidence that pulsed electrical stimulation of peripheral or cranial nerves has beneficial effects as adjunct therapy for clinical states such as partial complex epilepsy, generalized epilepsy, urinary urge incontinence, Alzheimer's disease, inappropriate sinus tacycardia, neurogenic pain, depression, and refractory angina etc.

Nerve and muscle cells have membranes that are composed of lipids and proteins, and have unique properties of excitability such that an adequate disturbance of the cell's resting potential can trigger a sudden change in the membrane conductance. Under resting conditions, the inside of the nerve cell (neuron) is approximately −90 mV relative to the outside. As shown in FIG. 1, a neuronal process can be divided into unit lengths, which can be represented in an electrical equivalent circuit. Each unit length of the process is a circuit with its own membrane resistance ($r_m$), membrane capacitance ($c_m$), and axonal resistance ($r_a$).

A nerve cell can be excited by increasing the electrical charge within the nerve, thus increasing the membrane potential inside the nerve with respect to the surrounding extracellular fluid. This fundamental feature of the nervous system i.e., its ability to generate and conduct electrical impulses, can take the form of action potentials, which are defined as a single electrical impulse passing down an axon. This action potential (nerve impulse or spike) is an "all or nothing" phenomenon, (shown schematically in FIG. 2), that is to say once the threshold stimulus intensity is reached, an action potential will be generated. As shown in the Figure, stimuli 1 and 2 are subthreshold, and do not induce a response. Stimulus 3 exceeds a threshold value and induces an action potential (AP) which will be propagated. The information in the nervous system is coded by frequency of firing rather than the size of the action potential. The threshold stimulus intensity is defined as that value at which the net inward current (which is largely determined by Sodium ions) is just greater than the net outward current (which is largely carried by Potassium ions), and is typically around −55 mV inside the nerve cell relative to the outside (critical firing threshold). If, however, the threshold is not reached, the graded depolarization will not generate an action potential and the signal will not be propagated along the axon.

As shown in FIG. 3, the resulting membrane voltage change will affect adjacent portions of the membrane, and in a nerve, that will propagate as a nerve impulse. In FIG. 3 the impulse is traveling from right to left. Immediately after the spike of the action potential there is a refractory period when the neuron is either unexcitable (absolute refractory period) or only activated to sub-maximal responses by suprathreshold stimuli (relative refractory period). The absolute refractory period occurs at the time of maximal Sodium channel inactivation while the relative refractory period occurs at a later time when most of the Sodium channels have returned to their resting state by the voltage activated Potassium current. The refractory period has two important implications for action potential generation and conduction. First, action potentials can be conducted only in one direction, away from the site of its generation, and secondly, they can be generated only up to certain limiting frequencies.

Most nerves in the human body are composed of thousands of fibers, of different sizes designated by groups A, B and C, which carry signals to and from the brain. For example, a major nerve such as the Vagus nerve may have approximately 100,000 fibers of the three different types each carrying signals. Each axon (fiber) of that nerve conducts only in one direction, in normal circumstances. The A and B fibers are myelinated (i.e., have a myelin sheath, constituting a substance largely composed of fat), whereas the C fibers are unmyelinated.

Components of nerve stimulation systems include electrodes next to the nerve bundle or wrapped around the nerve and a lead with conductor connected to a pulse generator. Functional electrical stimulation realizes the excitation of the nerve by directly injecting charges into the nerve via the electrodes. The electrical field, necessary for the charge transfer, is simply impressed via the wires of the electrodes.

The power supply can be implanted, as in a cardiac pacemaker, or alternatively, there may be an implanted lead-receiver and an external transmitter, with their respective coils being inductively coupled. The implantable lead-receiver can be miniaturized utilizing the currently available electronic technology. Alignment of the subcutaneous coil-receiver and external coil-transmitter is critical for effective electromagnetic coupling. Since the receiver and transmitter coils are coupled, the degree of coupling depends, in part, upon the physical spacing between the coils and how they are placed with respect to each other (orientation). Such issues do not normally occur when a direct electrical connection is made between the pulse source and the stimulating electrodes.

The system described in this invention provides improved means for proximity sensing to aid in the optimal placement of the external-transmitting coil. Furthermore, it provides the means for continuous feedback regulation of output pulses, as the two coils shift relative to each other, in the course of activities during the day or night during sleep.

It should be obvious to one skilled in the art that various sensor modalities such as Hall effect, ultrasonic, inductive, capacitive etc. can be considered for proximity sensing. The Hall effect sensor opens and closes a circuit electronically based on changes in magnetic flux between the sensor and a target. This sensor can provide rotation speed or position measurement. The ultrasonic sensor emits an ultrasonic pulse that reflects back from an object entering the sonic cone. The time of reflection of the signal (dependent in part on the ultrasonic reflectivity of materials) provides a measure of the distance of the sensor from an object. An inductive proximity sensor consists of a coil and ferrite arrangement, an oscillator and detector circuit and a solid-state output. The oscillator of the inductive proximity sensor creates a high frequency field radiating from a coil in front of the sensor. A metallic object can enter the field and have eddy currents induced and detected from its surface. The capacitive sensor detects the approach of a target near its leading surface and this results in an increase in the capacitance. The increased capacitance results in the increase of amplitude of an oscillatory signal which can be detected. A GMR sensor was used in this embodiment as it affords large separation between the two coils across various mediums. This sensor uses magnetic field strength and direction of the magnetic field to provide relatively accurate location measurement of a magnetic material or target. The size of the sensor and associated circuitry are also quite favorable in this case.

The prior art addresses proximity sensing but not with the methodology disclosed here, and not with an implanted device with passive circuitry. The Mann U.S. Pat. No. 5,545,191 discloses a transcutaneous coupling device having an implanted unit and an external unit using Velcro® for attaching the external unit to the skin in a proper location for optimal electromagnetic coupling between the units.

U.S. Pat. No. 5,314,453 (Jeufter) is directed to position sensitive power transfer between an implanted power supply and a magnetic field sensing device. In this patent, a magnetically operated reed switch opens when the field from the magnet is remote or misarranged to prevent transmission of high frequency power by the transmitter antenna coil. Whereas the object of this patent is to either deliver or not deliver power to the implanted power source, the primary objective of the present invention is to regulate the output to the passive lead-receiver, thereby regulating the amount of current delivered to nerve for stimulation.

U.S. Pat. No. 5,811,893 (Soyck) applies a second sensor to react to the interference fields in order to maintain the signal through the feed-forward loop and preserving the functional state of the approximation switch even in the case of magnetic field interference.

U.S. Pat. No. 4,352,960 (Dormer) and U.S. Pat. No. 4,736,747 (Drake) merely disclose transcutaneous coupling by magnetically securing the subcutaneous and supercutaneous members.

U.S. Pat. No. 5,117,825 (Grevious) is directed to radio frequency coupling between an external programmable component and an implanted cardiac pacemaker for the purpose of programming the implanted device.

SUMMARY OF THE INVENTION

The present invention comprises a transcutaneous signal coupling method and apparatus for detecting the position of a passive, implanted electrode and transferring an electric excitation signal to the electrode from an external source. The apparatus of the invention includes an external unit containing a power source, a pulse generation circuit, a proximity sensing circuit, an inductive coil, and an implanted or internal unit. The internal unit contains a small magnet composed of materials, such as Samarium-Cobalt, that exhibit Giant Magneto-resistor characteristics, a passive receiving circuitry and an inductive coil. These Magneto-resistor sensors overcome a weakness in conventional resistor and Hall effect sensors with good sensing under relatively large separation between the sensor and the target magnet. The sensor of the invention measures the direction of the field applied from the magnet to the sensor within a specific range of field strength magnitude.

In accordance with a feature of this invention, the condition where the supercutaneous primary coil comes in optimal proximity and is located in parallel to the secondary subcutaneous coil, along its axis, can be recorded. An indicator provides measure of the proximity distance. The external unit has indicators for low battery, no output state, failure condition etc. These indicators are mounted in the remote external package. The intent of the present invention is to provide the user with detailed information concerning the state of the system while in use.

In another feature of this invention, as the axis or distance between the primary and secondary coils changes, the output of the external circuit provides a signal for correction, thereby providing feedback regulation of the current that is delivered to the implanted passive lead-receiver.

Various other features, objects and advantages of the invention will be made apparent from the following description taken together with the drawings.

BRIEF DESCRIPTION OF THE DRAWINGS

The drawings illustrate the best mode presently contemplated of carrying out the invention.

In the drawings.

Figure 1:
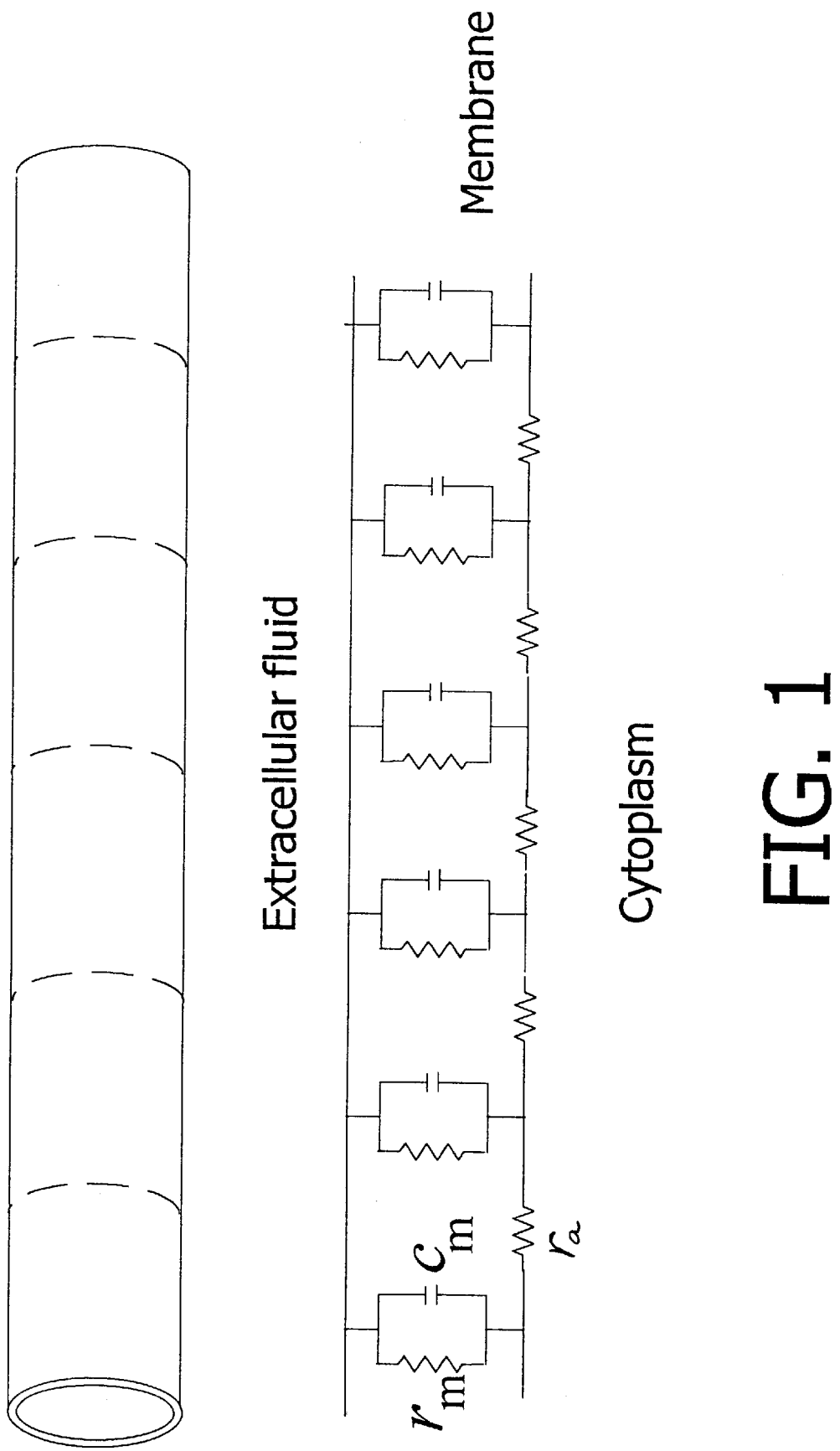
FIG. 1 is a schematic of the electrical equivalent circuit of the membrane of excitable cells.
Figure 2:
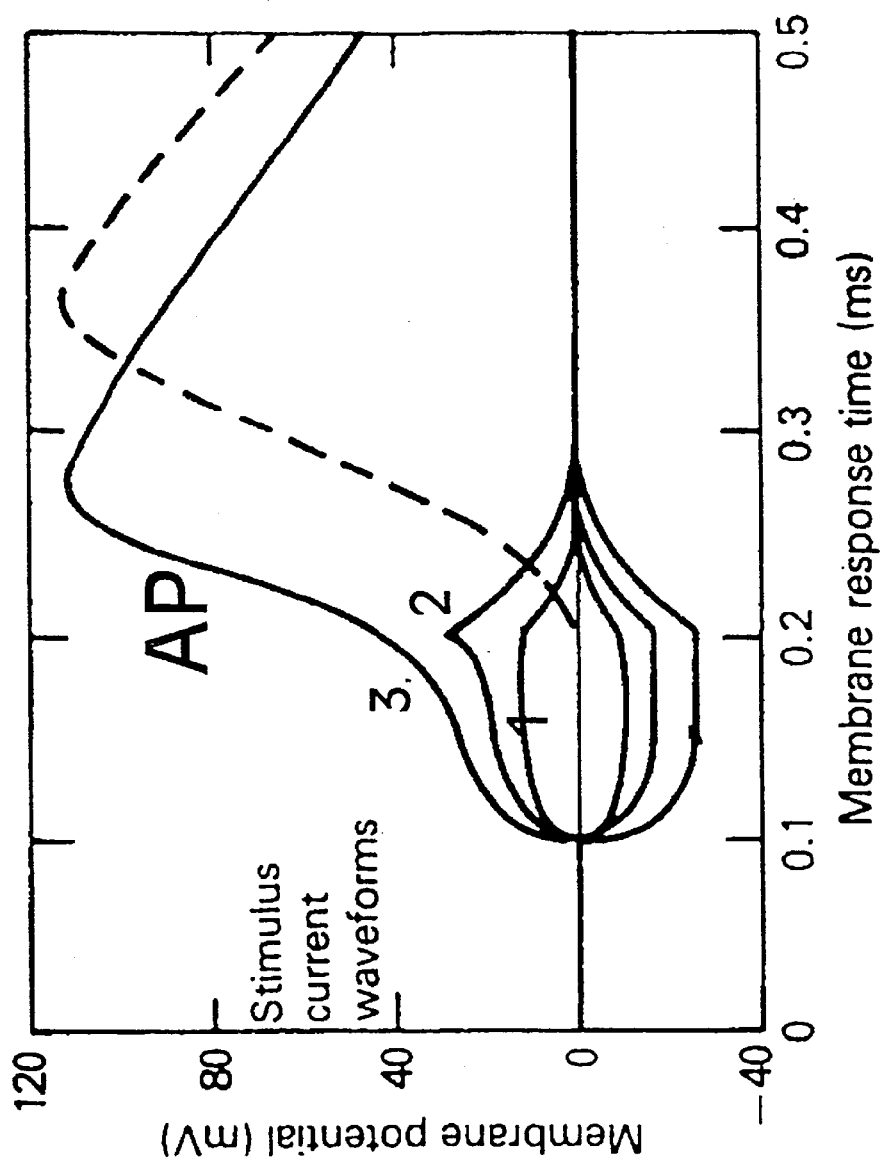
FIG. 2 shows schematic of an action potential.
Figure 3:
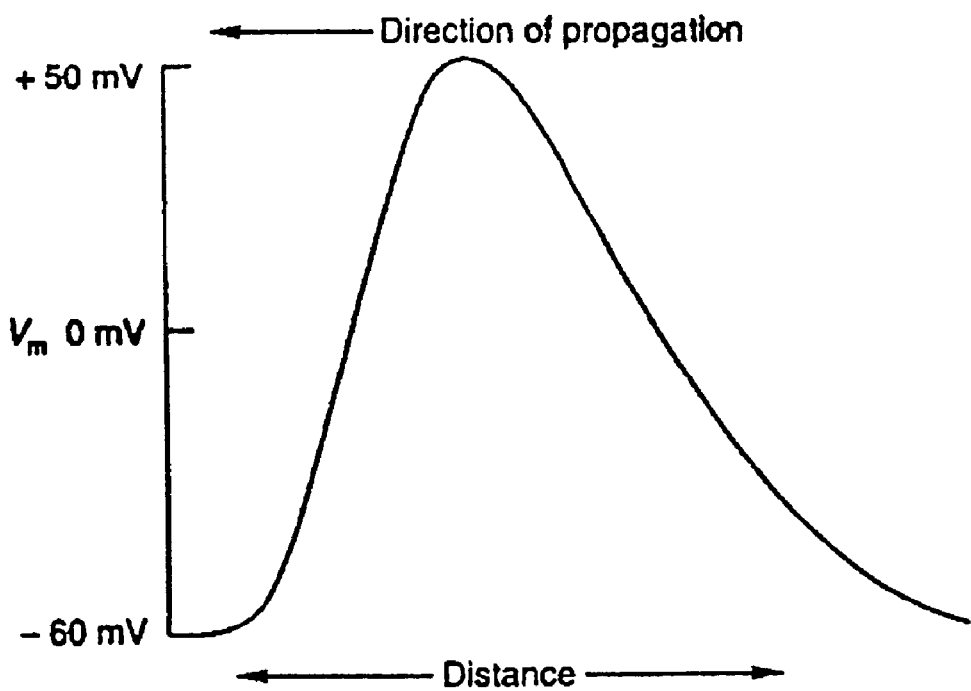
FIG. 3 shows propagation of a nerve impulse.
Figure 3:
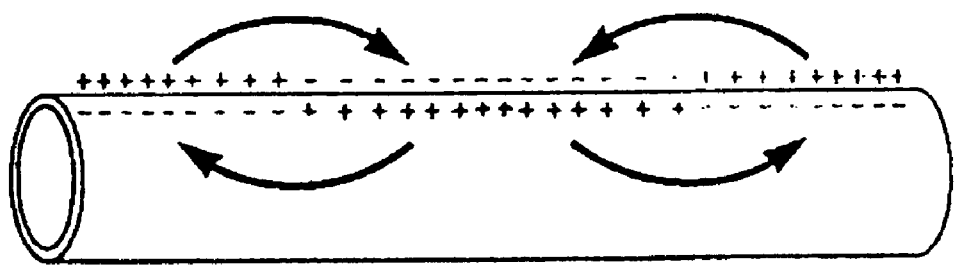

The following are reference numbers in the drawings:
1. subthreshold nerve stimulus
2. subthreshold nerve stimulus
3. suprathresthold nerve stimulus
38. skin
40. control logic for magnitude, frequency and pulse-width
42. pulse generation logic
44. differential amplifier
45. feed-forward signal from pulse generation circuit to external coil
46. proximity sensing circuit
47. temperature compensation circuit
48. proximity sensing unit
49. communication link between external coil and remote external circuitry
50. primary inductive coil (external)
51. cable to the external device
52. secondary coil that is subcutaneous (embedded)
53. magneto-resistor or GMR magnet
54. electrode wire
55. electrode (cathode)
56. programmable logic
57. remote external circuitry and power supply unit package (external stimulator)

58. battery unit (pack)
59. body part to be stimulated
62. indicator unit
63. audio alarm
64. programming unit
70. voltage controlled oscillator (VCO) block
72. output buffer block
76. initialization circuit block
78. phase locked loop (PLL) phase comparator block
80. PLL comparison frequency divider
82. PLL reference frequency divider
83. PLL synthesis oscillator block
84. PLL crystal oscillator block
86. PLL control unit block
94. oscillator capacitor 1, 69 pF
96. reference crystal, 2 MHz
98. oscillator capacitor 2, 30 pF
100. oscillator variable capacitor, 60 pF
102. transistor base resistor, 100K
104. transistor, 2SC1906
106. variable inductor coil, 7S144
108. transistor emitter capacitor, 10 pF
110. transistor base capacitor, 1 $\mu$F
112. transistor base capacitor, 1 $\mu$F
114. transistor emitter capacitor, 1 $\mu$F
116. transistor emitter resistor, 1 K$\Omega$
118. transistor emitter capacitor, 100 pF
120. variable capacitance diode, 1SV123
122. transistor emitter resistor, 47 K$\Omega$
124. variable capacitance diode, 1SV123
126. frequency to voltage resistor, 47 K$\Omega$
128. frequency to voltage resistor, 2.2 K$\Omega$
130. frequency to voltage capacitor, 10 $\mu$F
132. frequency to voltage resistor, 2.2 K$\Omega$
134. feedback capacitor, 0.01 $\mu$F
136. output buffer capacitor, 0.01 $\mu$F
138. output buffer resistor 10 K$\Omega$
140. field effect transistor, 2SK439
142. output capacitor, 0.001 $\mu$F
144. variable inductor coil, 7S144
145. complete PLL circuit with regulation
152. variable capacitor, approx. 500 pF
154. bridge diode rectifier
156. bridge resistor, 100$\Omega$
158. capacitor, 1000 pF
160. switch
162. current limiting diode
164. output resistor, 10 K$\Omega$
165. electrode body connection (cathode)
166. output capacitor, 0.22 $\mu$F
167. implant (secondary) circuit
169. return electrode connection (Anode)
170. resistor, 1 K$\Omega$
172. zener diode
174. resistor, 12 K$\Omega$
176. resistor, 1 K$\Omega$
178. variable resistor, 5 K$\Omega$
180. resistor, 1 K$\Omega$
182. resistor, 12 K$\Omega$
184. resistor, 1 K$\Omega$
185. amplifier output connector
186. operation amplifier
188. operational amplifier
190. operational amplifier
192. resistor, 68 K$\Omega$
194. operational amplifier
195. resistor, 3.9 K$\Omega$
196. resistor, 98 K$\Omega$
198. sensor 1, Siemens GMR C6
200. resistor, 1 K$\Omega$
202. sensor 2, Siemens GMR C6
204. resistor, 1 K$\Omega$
206. resistor, 3.3 K$\Omega$
208. resistor, 10 K$\Omega$
210. operation amplifier
220. resistor, 120 K$\Omega$
222. capacitor, 3.3 $\mu$F
224. transistor, 2SC1815
226. resistor, 8.2 K$\Omega$
227. program reset
228. NAND gate, 74LS00
230. NAND gate, 74LS00
232. NAND gate, 74LS00
234. JK Flip Flop, 74LS73
236. NAND gate, 74LD00
238. diode, 1S1588
240. resistor, 1 K$\Omega$
241. capacitor, 0.47 $\mu$F
capacitor, 0.47 $\mu$F
244. NAND gate, 74LS00
245. resistor, 1 K$\Omega$
246. diode, 1S1588
247. multivibrator
248. NAND gate, 74LS00
250. NAND gate, 74LS00
252. inverter, 74LS04
253. clock output of initialization circuit
254. NAND gate, 74LS00
256. inverter, 74LS04
257. load enable from initialization circuit
258. inverter, 74LS04
260. NAND gate, 74LS00
262. inverter, 74LS04
264. NAND gate, 74LS00
266. NAND, 3 input gate, 74LS10
267. programmable data port
268. NAND, 3 input gate, 74LS10
270. NAND, 3 input gate, 74LS10
271. data output from initialization circuit
272. multiplexer/switch, CD4067B
274. multiplexer/switch, CD4067B
276. NAND gate, 74LS00
278. 4 bit binary counter, 74LS93 (programmable counter)
280. JK flip flop, 74LS73
282. inverter, 74LS04
284. NAND gate, 74LS00
286. JK flip flop, 74LS73
288. JK flip flop, 74LS73

DETAILED DESCRIPTION OF THE INVENTION

The following description is of the current embodiment for carrying out the invention. This description is not to be taken in a limiting sense, but is made merely for the purpose of describing the general principles of the invention. The scope of the invention should be determined with reference to the claims.

Figure 4:
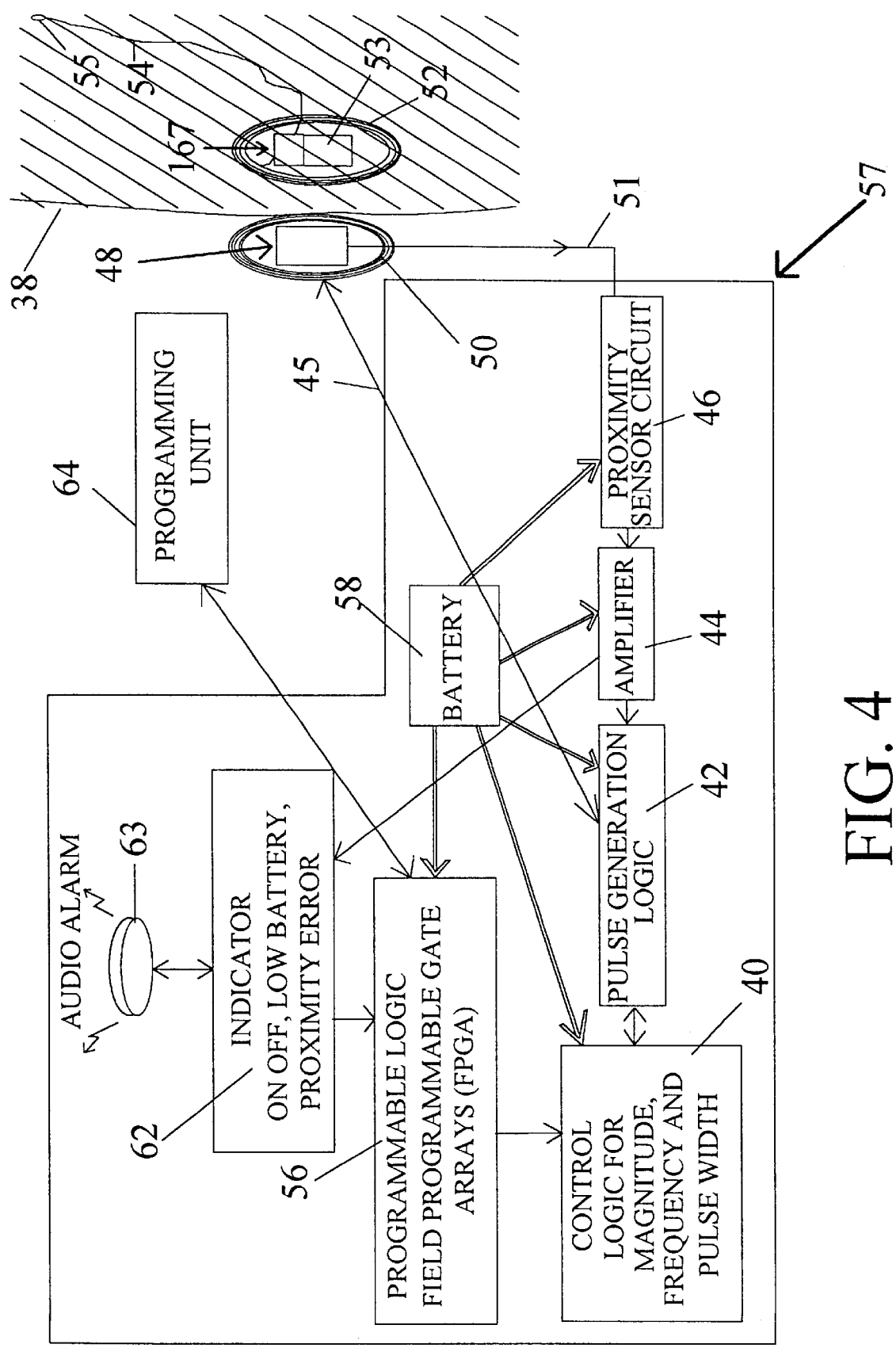
FIG. 4 is a generalized block diagram of the invention, including the main components of the invention such as the pulse generator, programmable circuit, coils, proximity sensor, indicators and battery unit.

FIG. 4 shows an overall block diagram of the invention with an external coil 50, a proximity sensing unit 48, and a subcutaneous secondary coil 52 with a GMR magnet 53 associated with the proximity sensing unit 48. A proximity sensing circuit 46 provides feedback of the position of the secondary embedded coil 52. The signal output from proximity sensing circuit 46 is derived from the relative location of the coils 50 and 52. The coil sub-assemblies consist of the coil and the associated electronic components that are rigidly connected to the respective coil. This signal from the proximity sensing circuit 46 is provided to the pulse generation logic 42 through amplifier 44 and this signal varies to compensate for any variation of the nominal signal from proximity sensing circuit 46. The programmable parameters are stored in a programmable logic 56. These parameters are provided to the control logic 40, for magnitude, frequency and pulse-width control. The battery (chargeable or disposable) 58 is necessary to provide power to all other devices such as the control logic for magnitude, frequency and pulse width 40, the pulse generation logic 42, the differential amplifier 44, the proximity sensing circuit 46, the programmable logic 56, the proximity sensing unit 48 and the indicator unit 62. The output of the pulse generation logic 42 is provided to the external coil 50 as indicated by arrow 45. The sensor and associated circuit present in the proximity sensing unit 48 and the external coil 50 are placed in a supercutaneous manner. The set of external components shown in FIG. 4 are installed in the remote external circuitry package 57.

A voltage controlled oscillator (VCO) 70 (shown in FIG. 5) is utilized to generate an electrical excitation pulse of a pre-determined (programmable) frequency. The frequency can be changed by a phase locked loop (PLL) control signal applied to VCO block 70. The theoretical range of the pulse frequency is quit large with values from 10 to 120 MHz. This excitation pulse signal from the primary coil 50 is inductively coupled with the secondary coil 52 for approximately up to 25 mm separation between coils. The pulse signal is induced in the secondary coil 52, and then the waveform is shaped for an adequate signal delivered to excitable tissue 59, such as a nerve bundle, by the implanted electrode 55 positioned in contact with the tissue. The separation between the coils 50 and 52 can vary and the signal produced at the secondary coil 52 is maintained consistent within design parameters. The proximity sensors 198, 202 detect the presence of a GMR (Giant Magneto-Resistor) magnet 53, composed of Samarium Cobalt and is rigidly attached to the secondary subcutaneous coil 52. The proximity sensors 198, 202 are mounted externally as a rigid assembly and sense the actual separation between the coils, also known as the proximity distance. Adjustment of the parameters of the VCO 70 is possible in order to compensate for variations in the primary and secondary coil separation. In the event the distance exceeds the theoretical limit, an alarm will sound to indicate the failure to produce an adequate signal in the secondary implant circuit 167, as applied in the present embodiment of the device.

Figure 5:
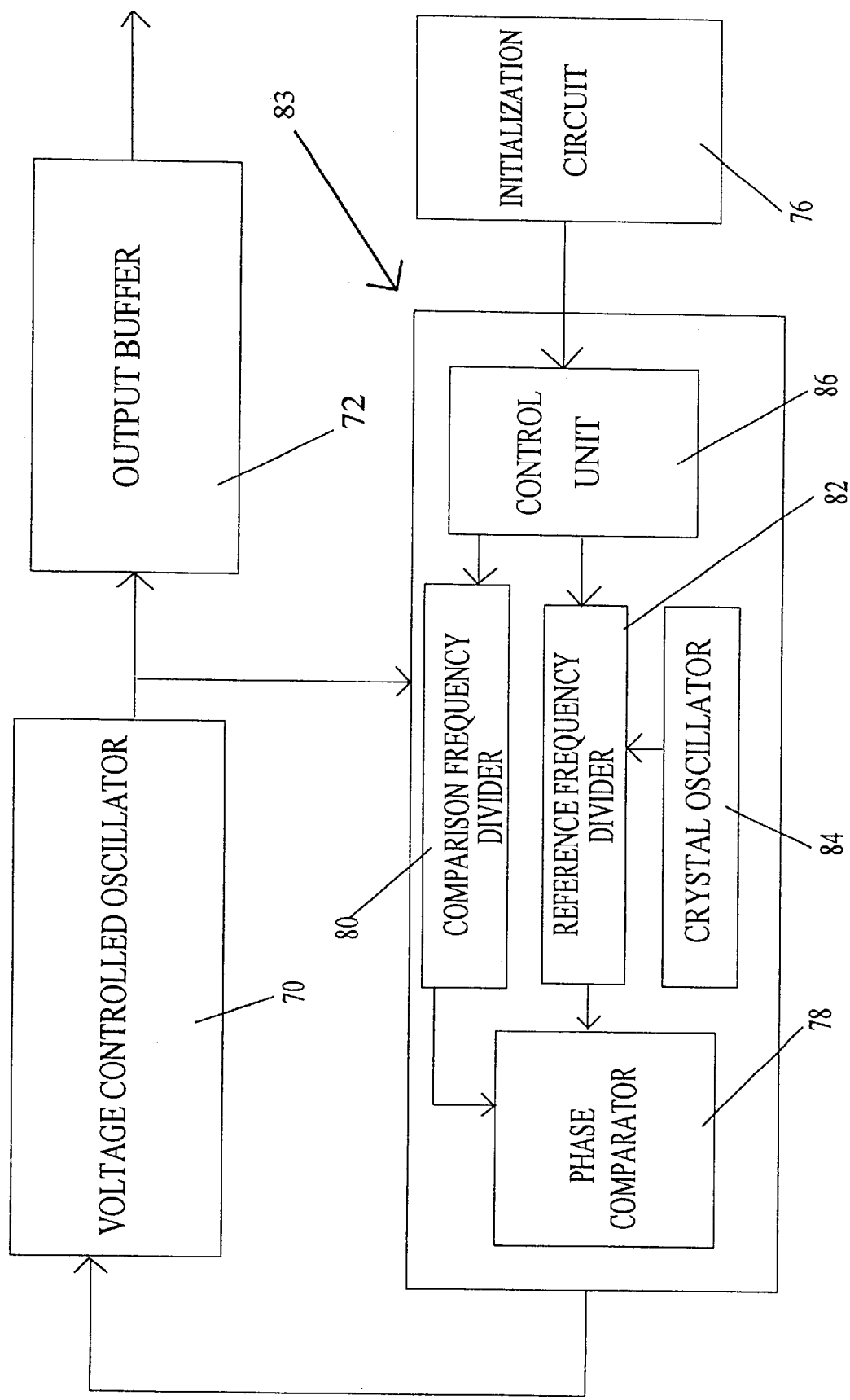
FIG. 5 is a block diagram of the phase locked loop based pulse generator.
Figure 6:
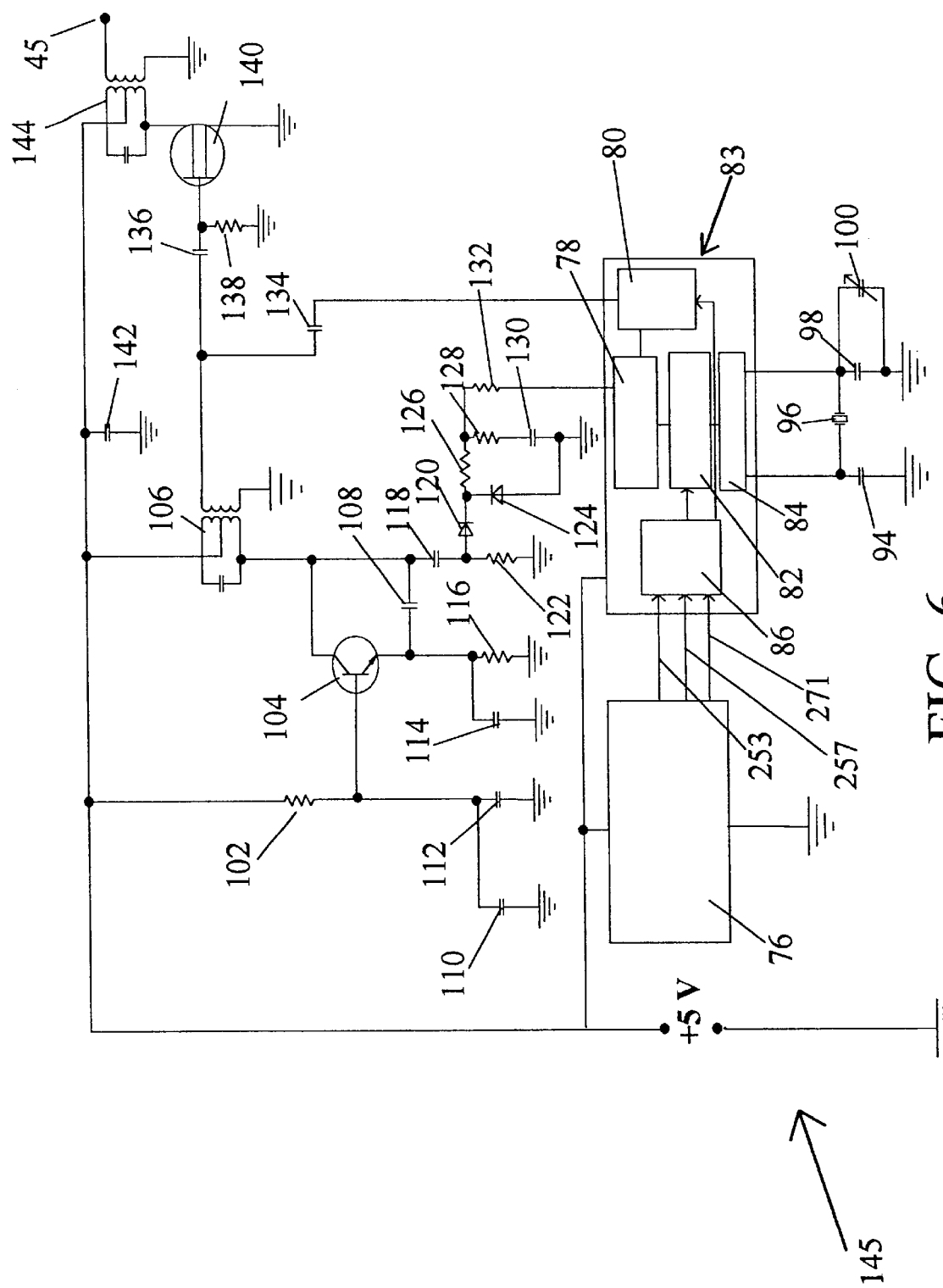
FIG. 6 provides greater details of the diagram shown in FIG. 5, such as the electronic components used in the high frequency signal generation.

Referring to FIGS. 5 and 6, a phase locked loop synthesizing oscillation circuit 83 is used to produce a pulse of accurate frequency, the value of which is selectable. The circuit 83 compares frequency of the reference frequency source with the frequency of the signal actually produced by the VCO 70. The oscillator circuit 83 adjusts for the change in actual frequency and controls the actual frequency to match the reference frequency. The change in the frequency is affected by changing the value of a frequency divider constant of the reference frequency and the comparison frequency components respectively. The oscillator frequency is affected by adjusting values of the variable capacitance diodes 120, 124 and transistor emitter capacitor 118. The combination of resistor and capacitor components 126, 128, 130, 132 is used to convert the pulse signal originating from the charge pump of the synthesizing oscillator 83, to a voltage value that adjusts for the frequency generated by complete PLL circuit 145, by varying the capacitance of variable capacitance diodes 120, 124. It will be obvious to one skilled in the art that, alternately, a direct voltage signal can be applied to the VCO 70 to bypass the above components to thus provide the appropriate frequency control. In another version of this circuit, the signal obtained from the proximity sensor circuit 46 (FIG. 4) can be applied to the VCO 70 to control the frequency of the signal. A Field Effect Transistor device 140 is used as an output buffer to isolate the external devices and to adjust the level of output signal.

A highly stable crystal oscillator 96 is used as the frequency reference, as shown in FIG. 6. The crystal oscillator 96 provides a signal with a stable frequency for comparison with the frequency of comparison signal, obtained by feedback of the output of capacitor 134. A phase comparator 78 is used to compare the actual signal frequency produced with the reference frequency, and adjusts the signal from the control unit 86 to reduce the difference of both frequencies to zero. A programmable counter 278 (shown in FIG. 7) is used to reduce the output frequency by a fraction. The phase comparison 78 function is provided by the PLL synthesis oscillator (PSO) 83. In this version of the circuit, this device is chip # MB87014A 83 available from Motorola Corp., alternatively, a functionally equivalent version of this chip can be utilized. The oscillator 83 detects the difference of the phase comparison frequency and reference frequency signals, after appropriate division, and a phase difference signal is output to the VCO 70, as a pulse signal of appropriate frequency. The programming of the frequency division circuit is provided by serial 16 bit data at the data port of the PSO 267, also shown as Programmable Data in FIG. 7. This data is read on the rising edge of the clock signal from a 2 MHz crystal oscillator 96, for this embodiment. A high-value at the load enable 257 at its connector, allows either the comparison or reference side of the divisor to be set as per the control bit on the data line. When the 16 bits of data are all at logic low, the PLL circuit output 271 stops normal operation and no signal is provided. This state is enabled for "no pulse signal generation" condition. The clock signal for frequency divider values setup is obtained from clock output connection of initialization circuit 253. The initialization circuit is utilized for setting the frequency dividers at power-up, but a serial update can be made to the programmable data port 267 at run time. The output voltage level of the pulse signal is of the range of 0 V to the power input supply voltage, (typically 5V). The advantage of the PLL circuit 83 is that a signal of stable high frequency is possible by referencing it at lower frequency levels using appropriate division of the high frequency VCO 70 signal and reference signal.

Figure 7:
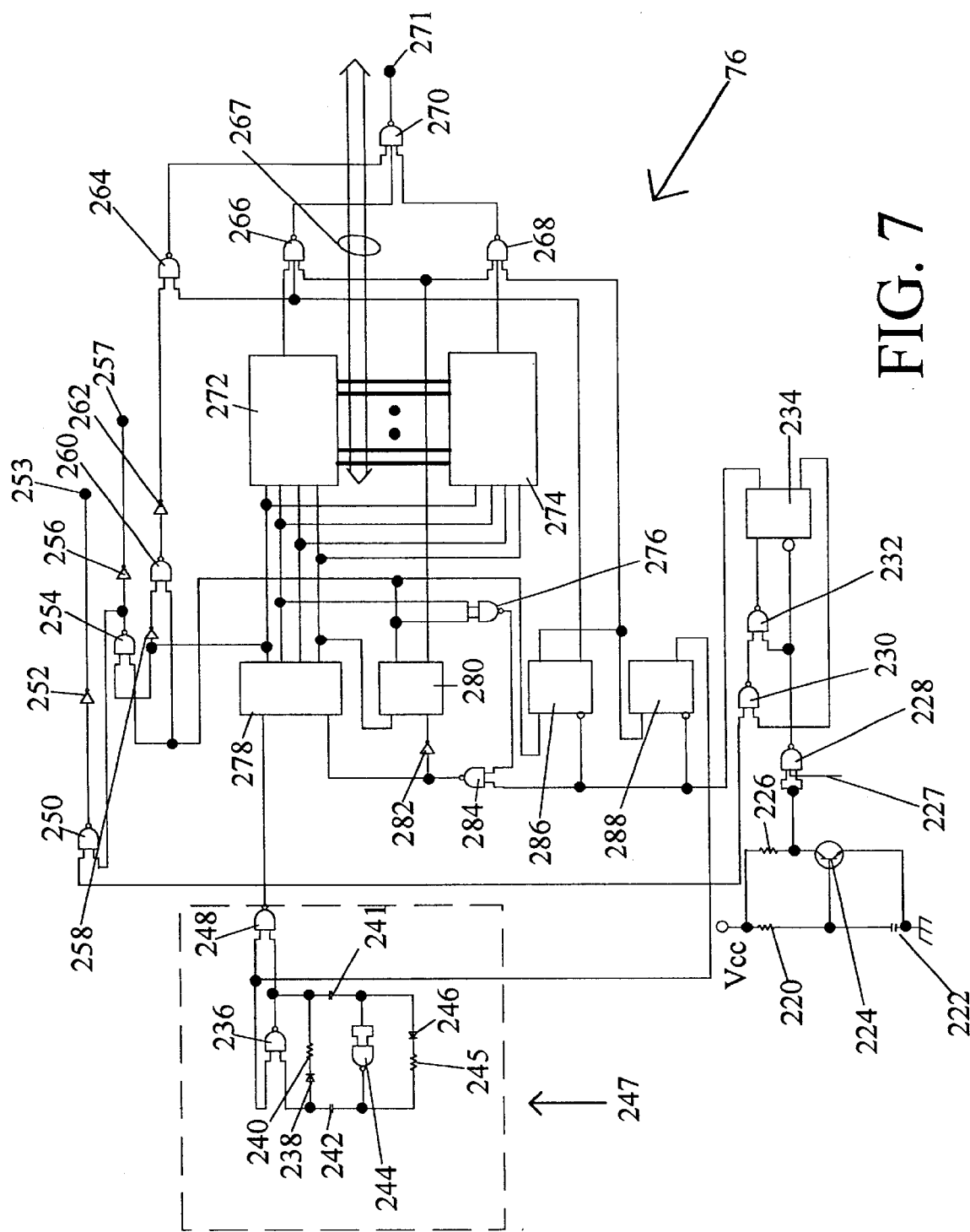
FIG. 7 shows the electronic components used in the frequency selection and initialization stage.

The initialization circuit 76, shown in FIG. 7, depicts a circuit whose function is to provide dividing ratio setting data to the PLL 83, after turning on or after a program reset signal is applied. The capacitor 222 charges to a threshold value at the base of transistor 224 and enables the pulse signal generated by the multi-vibrator 247 to be conducted by enabling the Flip Flop 234. The multi-vibrator 247 (including logic components 236, 238, 240, 241, 242, 244, 245, 246), provide a signal of approximately 600 Hz frequency for control of other signals in this circuit. The data is present at the data lines multiplexed at the NAND gate 270 and a data output 271 from initialization circuit 76. The load enable from initialization circuit 257 provides the signal to load this data and the control signal to the PLL 83 through its initialization circuit block 76. This step allows for the loading of the comparison frequency divider data, followed by the reference frequency divider data, during initialization and programming setup. A binary counter Device 278 is a 16 bit counter for multiplexing the divider data to output of NAND gate 270. The 16 bit divider data can be provided by pre-programmed storage of patterns in devices such as Field Programmable Logic Arrays 56. Other storage devices can be applied for the same operation. The circuit shown in FIG. 6 provides a pulse waveform of the appropriate characteristics, to the external (primary) inductive coil 50. This coil 50 is inductively coupled with secondary coil 52, implanted subcutaneously. The secondary coil 52 propagates this signal and the implanted circuit 167 converts it to an appropriate waveform that is delivered to the electrode 55.

Figure 8:
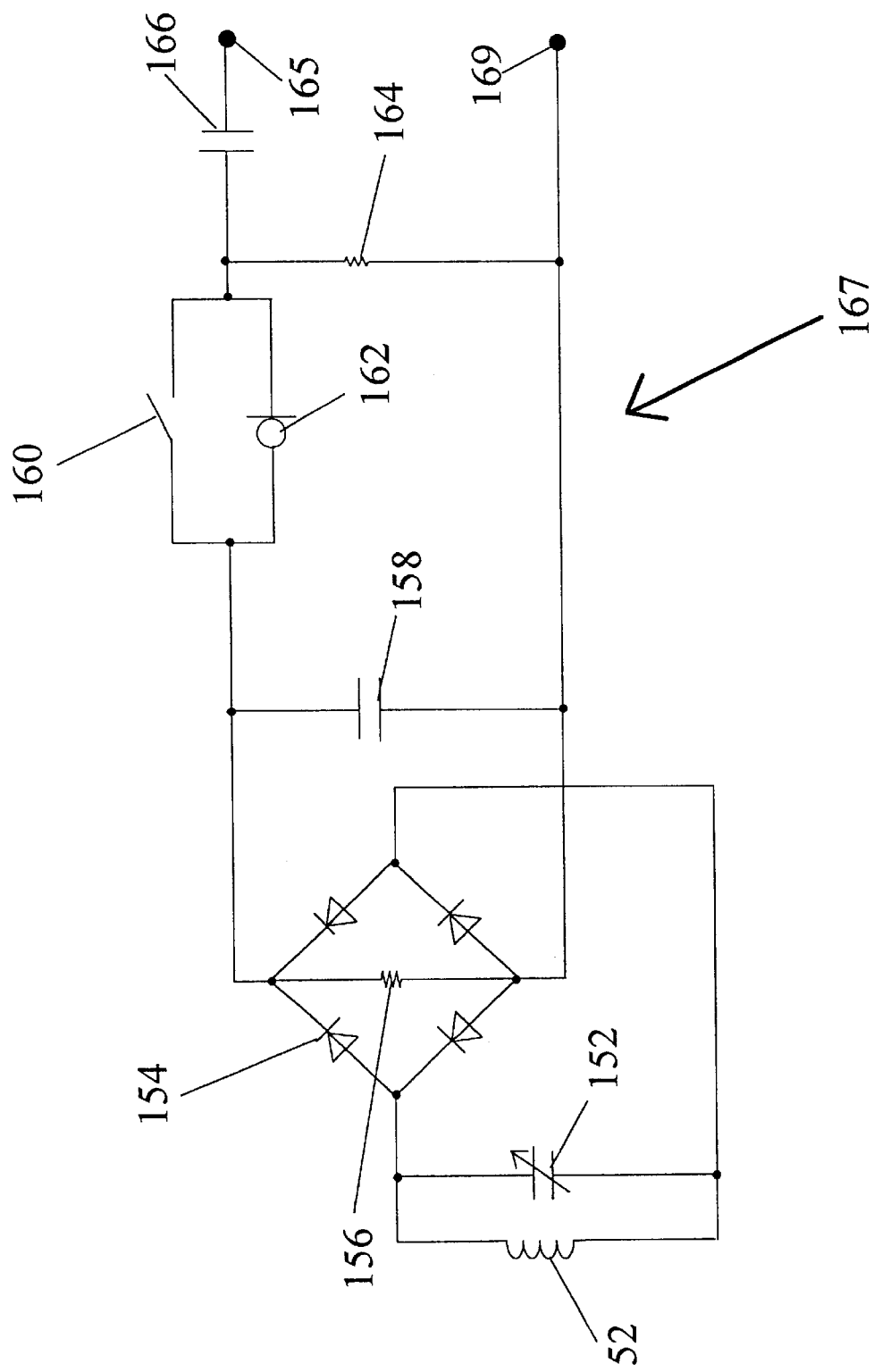
FIG. 8 shows the passive subcutaneous (implanted) circuit, which will couple with the external coil placed supercutaneously.

The circuitry of the implantable lead-receiver is shown in FIG. 8. This version of the circuit uses all passive components. In this embodiment, a 25 turn copper wire of 30 gauge thickness was used for both the primary coil 50 and secondary coil 52. This wire was concentrically wound with the windings all in one plane. A variable capacitor 152 provides flexibility in tuning to the actual frequency received by coil 52 from the primary coil 50. The frequency of the pulse-waveform delivered to embedded coil 52 can vary and so a variable capacitor 152 provides ability to tune the secondary implanted circuit 167 to the signal from the primary coil 50. The pulse signal from embedded coil 52 is rectified by the diode bridge 154 and frequency reduction obtained by capacitor 158 and resistor 164. The last component in line is capacitor 166, used for isolating the output signal from the electrode wire 54. The return path of signal from cathode 165 will be through the tissue for "Bipolar" stimulation. Alternatively, anode 169 can be connected to the remote ground connection of implantable circuit 167, providing for much larger intermediate tissue for "Unipolar" stimulation. The "Bipolar" stimulation offers localized stimulation of tissue compared to "Unipolar" stimulation, where skeletal muscles can be stimulated. The implanted circuit in this embodiment is passive, so a battery does not have to be implanted. It is however possible, in a future version, to implant a battery source for use of active component logic in the implant.

Figure 9:
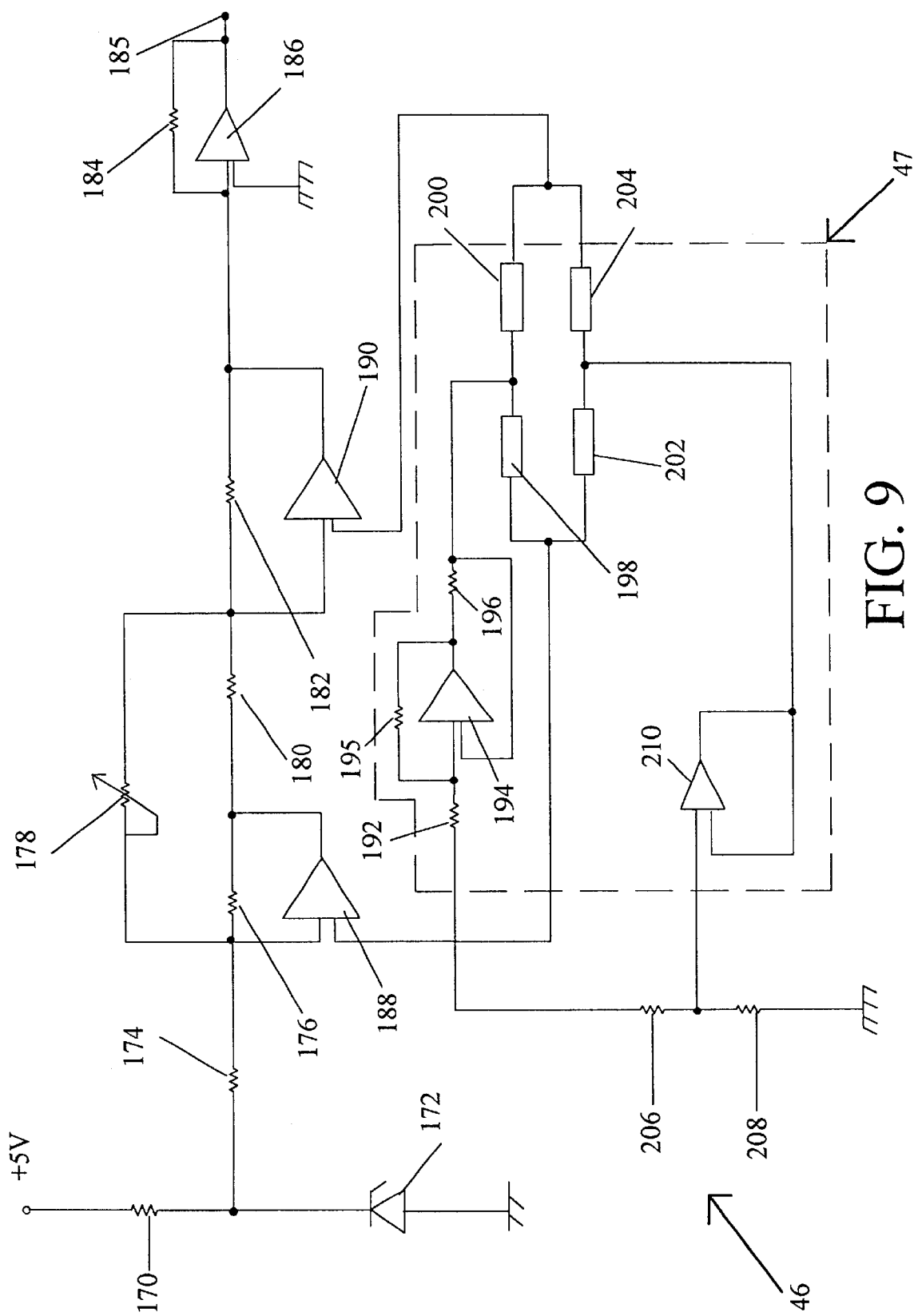
FIG. 9 shows the circuit used to drive the proximity sensors and also provides temperature compensation.

FIG. 9 shows the circuit used to drive the proximity sensors. The two sensors 198, 202 obtain their feedback from the GMR magnet 53 that is implanted. This circuit also provides temperature compensation, shown in the temperature compensation circuit 47 of FIG. 9. The sensors 198, 202 are 'Giant Magneto Resistor' (GMR) type sensors packaged as proximity sensing unit 48. The resistance effect depends on the combination of the soft magnetic layer of magnet 53, where the change of direction of magnetization from external source can be large, and the hard magnetic layer, where the direction of magnetization remains unchanged. The typical change in resistance due to the GMR effect can be about 5% of the nominal resistance. The resistance of this sensor varies along a straight motion through the curvature of the magnetic field. A bridge differential voltage is suitably amplified and used as feedback for appropriate compensation.

The Siemens GMR B6 (Siemens corp. Special components Inc. New Jersey) can be used for this function. The maximum value of the peak-to-peak signal is observed as the external magnetic field becomes strong enough, at which point the resistance increases, resulting in the increase of the field-angle between the soft magnetic and hard magnetic material. The bridge voltage also increases. In this application, the two sensors 198, 202 will be oriented orthogonal to each other.

The distance between magnet 53 and sensor is not relevant as long as the magnetic field is between 5 and 15 KA/m, and provides a range of distances between the sensors 198, 202 and the magnetic material. The GMR sensor registers the direction of the external magnetic field. A typical magnet to induce permanent magnetic field can be approximately 15 by 8 by 5 mm$^3$, for this application. However, this sensor is sensitive to temperature, such that the corresponding resistance drops as temperature increases. This effect is quite minimal until about 100° C. A full bridge circuit can be used for such compensation as shown in temperature compensation circuit 47 of FIG. 9. The sensors 198, 202 and a pair of resistors 200, 204 are shown as part of the bridge network for temperature compensation. It is also possible to use a full bridge network of two additional sensors in place of the resistors 200, 204. The bridge output is further amplified for this application.

The signal from either proximity sensor 198 or 202 is rectangular if the surface of the magnetic material is normal to the sensor and is radial to the axis of a circular GMR device. This indicates a shearing motion between the sensor and the magnetic device. When the sensor is parallel to the vertical axis of this device, there is a fall off of the relatively constant signal at about 25 mm. separation. The GMR sensor combination varies its resistance according to the direction of the external magnetic field, thereby providing an absolute angle sensor. The position of the GMR magnet can be registered at any angle from 0 to 360 degrees. The characteristics of the feedback signal from the proximity sensor will be developed separately.

Figure 10:
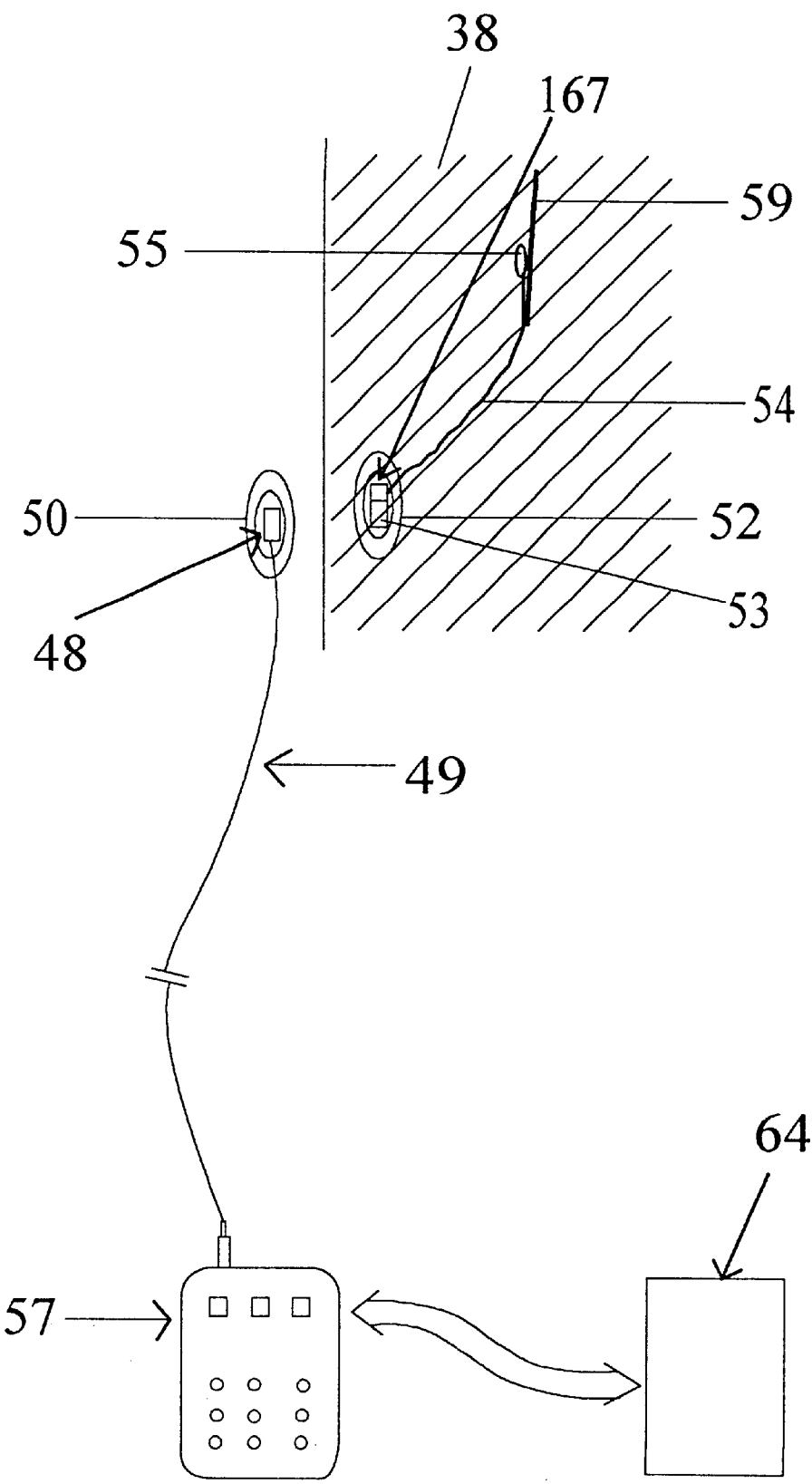
FIG. 10 shows the typical placement of the device in a clinical application.

The remote circuit package is shown in FIG. 10 and an indicator unit 62 (FIG. 4) is provided for: Low Battery (if external battery is low), program number in use, proximity distance too large or proximity failure (in case the patch containing the external coil 50, has been removed, or is twisted abnormally etc.) Indication is also provided to assist the placement of the patch. In case of general failure, a red light with audible signal is provided when the signal is not reaching the subcutaneous circuit. The information on the low battery, normal and out of power conditions will forewarn the user of the requirements of any corrective actions. Other information like the parameters of the program being applied and the normal operation of the device can be displayed as components of remote external circuitry and power supply unit 57. The battery 58 present in the remote external circuitry 57 can be completely recharged or replaced.

The methodology and apparatus described here, aids in the optimal positioning of the external coil and once the external coil is secured at the appropriate position, this invention ensures continuous feedback regulation of the signal pattern output to the body part to be stimulated.

The present invention may be embodied in other specific forms without departing from the spirit or essential attributes thereof. It is therefore desired that the present embodiment be considered in all aspects as illustrative and not restrictive, reference being made to the appended claims rather than to the foregoing description to indicate the scope of the invention.

Various alternatives and embodiments are contemplated as being within the scope of the following claims particularly pointing out and distinctly claiming the subject matter regarded as the invention.

We claim:

1. A method of proximity sensing and feedback regulation of stimulation pulses of an inductively coupled nerve or muscle stimulation system, comprising the steps of:
   a) providing an implanted stimulus receiver comprising a secondary coil with a magnet and circuitry;
   b) providing an external stimulator comprising a power source, electrical circuitry, and a primary coil; and
   c) providing proximity sensing means and control means comprising, a proximity sensor to sense the position of said primary coil in relation to said secondary coil, and control circuitry for feedback regulation of said stimulation pulses;

whereby, said stimulation pulses are regulated.

2. The method of claim 1, wherein said control circuitry comprises means for adjusting at least one variable component of the stimulation pulses selected from a group comprising current amplitude, frequency and pulse width.

3. The method of claim 1, wherein said proximity sensing means comprises at least two sensors to detect the magnetic field generated by said magnet.

4. The method of claim 3, wherein said at least two sensors are positioned orthogonally with respect to each other.

5. The method of claim 1, wherein said relative position of said primary coil to said secondary coil comprises at least one of the variables from a group comprising of distance, orientation, and displacement from axes between said primary coil and said secondary coil.

6. A method of proximity sensing between external and implanted coils of an inductively coupled nerve or muscle stimulation system, comprising the steps of:
 a) providing an implanted stimulus receiver comprising a secondary coil with a magnet and circuitry;
 b) providing an external stimulator comprising a power source, electrical circuitry, a primary coil, and indicator means; and
 c) providing at least two proximity sensors to sense the relative position of said primary coil to said secondary coil and indicate proximity on said indicator means;
 whereby, proximity of said primary coil and said secondary coil is sensed and indicated.

7. The method of claim 6, wherein said indicator comprises a visual indicator comprising of at least one light emitting diode.

8. The method of claim 6, wherein said indicator is an audio indicator.

9. The method of claim 6, wherein said magnet is composed of Samarium-cobalt.

10. The method of claim 6, wherein said at least two sensors detect the orientation of a magnetic field generated by said magnet.

11. The method of claim 6, wherein said sensors are positioned orthogonal to each other.

12. A system for proximity sensing and feedback regulation of stimulation pulses for an inductively coupled nerve or muscle stimulation system, comprising:
 a) an external pulse generator comprising a power source, electrical circuitry, and a primary coil;
 b) an implanted stimulus receiver comprising a secondary coil with a magnet and circuitry; and
 c) proximity sensing and control means comprising, a proximity sensor to sense the relative position of said primary coil to said secondary coil, and control circuitry for feedback regulation of the stimulation pulses responsive to said proximity sensor;
 whereby, said stimulation pulses are regulated.

13. The system of claim 12, wherein said relative position of said primary coil in relation to said secondary coil comprises at least one of the variables from a group comprising the distance, orientation, and displacement from axes between said primary coil and said secondary coil.

14. The system of claim 12, wherein, said control circuitry comprises means for adjusting at least one variable component of the stimulation pulses selected from a group comprising current amplitude, frequency and pulse width.

15. The system of claim 12, wherein the proximity sensing circuit includes at least two sensors to detect the orientation of a magnetic field generated by said magnet.

16. The system of claim 12, wherein said sensors are positioned orthogonal to each other.

17. The system of claim 12, wherein said magnet is composed of Samarium-cobalt.

18. A system of proximity sensing between external and implanted coils for an inductively coupled nerve or muscle stimulation system, comprising:
 a) an implanted stimulus receiver comprising a secondary coil with a magnet and circuitry;
 b) an external stimulator comprising a power source, electrical circuitry, a primary coil, and an indicator; and
 c) at least two proximity sensors to provide proximity signals to said electrical circuitry for proximity sensing based upon the relative position of the primary coil and secondary coil;
 whereby, the relative position of said primary coil with respect to said secondary coil is sensed and indicated on said indicator.

19. The system of claim 18, wherein said indicator comprises a visual indicator comprising of at least one light emitting diode.

20. The system of claim 18, wherein said indicator is an audio indicator.

21. The apparatus of claim 18, wherein said magnet is composed of Samarium-cobalt.

22. The apparatus of claim 18, wherein said at least two proximity sensors are positioned orthogonal to each other.

23. A method of regulating pulses to a nerve or muscle with an inductively coupled stimulation system having pulse generating means, a primary coil, and a subcutaneous secondary coil, comprising the steps of:
 a) providing a magnet with said secondary coil;
 b) providing proximity sensing means with said primary coil to sense the relative position of said primary coil to said secondary coil;
 c) providing a proximity sensing feedback circuit to determine the regulation required based on said relative position; and
 d) providing control logic circuitry to adjust the output regulation required;
 whereby said pulses delivered to said nerve or muscle are regulated.

24. The method of claim 23, wherein said proximity sensing means comprises at least two sensors.

* * * * *